United States Patent
Hartley et al.

(10) Patent No.: US 9,191,751 B2
(45) Date of Patent: Nov. 17, 2015

(54) MODULAR ADAPTER ASSEMBLY FOR TELECOIL AND AUXILIARY AUDIO INPUT DEVICE MIXING

(75) Inventors: Lee F. Hartley, Valencia, CA (US); Roger S. Meier, Canyon Country, CA (US); Glen A. Griffith, Newbury Park, CA (US); Tracey L. Kruger, Saugus, CA (US); R. Tissa Karunasiri, Valencia, CA (US); Scott A. Crawford, Castaic, CA (US); Frank Nigro, Valencia, CA (US)

(73) Assignee: Advanced Bionics AG, Staefa (CH)

( * ) Notice: Subject to any disclaimer, the term of this patent is extended or adjusted under 35 U.S.C. 154(b) by 173 days.

(21) Appl. No.: 13/983,563

(22) PCT Filed: Jan. 27, 2012

(86) PCT No.: PCT/US2012/022940
§ 371 (c)(1),
(2), (4) Date: Oct. 18, 2013

(87) PCT Pub. No.: WO2012/106206
PCT Pub. Date: Aug. 9, 2012

(65) Prior Publication Data
US 2014/0233775 A1 Aug. 21, 2014

Related U.S. Application Data

(60) Provisional application No. 61/439,669, filed on Feb. 4, 2011.

(51) Int. Cl.
*H04R 25/00* (2006.01)
*A61N 1/00* (2006.01)
*A61N 1/36* (2006.01)

(52) U.S. Cl.
CPC ............. *H04R 25/00* (2013.01); *H04R 25/43* (2013.01); *H04R 25/556* (2013.01); *H04R 25/558* (2013.01); *A61N 1/36032* (2013.01)

(58) Field of Classification Search
CPC .... H04R 25/556; H04R 25/558; H04R 25/30; H04R 25/305; H04R 25/554; H04R 25/60; H04R 25/505; H04R 2205/021; H04R 2205/63
USPC ............ 381/323, 328, 330, 312–321; 607/55, 607/56, 57
See application file for complete search history.

(56) References Cited

U.S. PATENT DOCUMENTS

| | | | |
|---|---|---|---|
| 4,947,432 A | 8/1990 | Topholm | |
| 6,775,389 B2 * | 8/2004 | Harrison et al. | 381/330 |
| 7,660,633 B2 * | 2/2010 | Darley et al. | 607/57 |
| 2004/0052391 A1 * | 3/2004 | Bren et al. | 381/331 |
| 2008/0288022 A1 * | 11/2008 | Van der Borght et al. | 607/57 |

FOREIGN PATENT DOCUMENTS

WO   WO-2005/062668   7/2005

OTHER PUBLICATIONS

International Search Report and Written Opinion received in International Application No. PCT/US12/022940 dated May 18, 2012.

* cited by examiner

Primary Examiner — Sunita Joshi
(74) Attorney, Agent, or Firm — ALG Intellectual Property, LLC

(57) ABSTRACT

An exemplary apparatus for use with an auditory prosthesis system includes a housing, a connector port disposed at least partially within the housing and configured to be communicatively coupled to an auxiliary audio input device, a telecoil disposed at least partially within the housing, and a multi-position switch disposed at least partially within the housing and configured to selectively enable the auxiliary audio input device and the telecoil. The auxiliary audio input device is enabled and the telecoil is disabled when the switch is in a first position, both the auxiliary audio input device and the telecoil are enabled when the switch is in a second position, and the telecoil is enabled and the auxiliary audio input device is disabled when the switch is in a third position. Corresponding apparatuses, systems, and methods are also disclosed.

13 Claims, 6 Drawing Sheets

MODULAR ADAPTER ASSEMBLY FOR TELECOIL AND AUXILIARY AUDIO INPUT DEVICE MIXING

RELATED APPLICATIONS

The present application claims priority to U.S. Provisional Patent Application No. 61/439,669 by Lee F. Hartley et al., filed on Feb. 4, 2011, and entitled "Modular Adapter Assembly for Telecoil and Auxiliary Audio Input Device Mixing," the contents of which are hereby incorporated by reference in their entirety.

BACKGROUND INFORMATION

The sense of hearing in human beings involves the use of hair cells in the cochlea that convert or transduce audio signals into auditory nerve impulses. Hearing loss, which may be due to many different causes, is generally of two types: conductive and sensorineural. Conductive hearing loss occurs when the normal mechanical pathways for sound to reach the hair cells in the cochlea are impeded. These sound pathways may be impeded, for example, by damage to the auditory ossicles. Conductive hearing loss may often be helped by the use of conventional hearing aids that amplify sound so that audio signals reach the cochlea and the hair cells. Some types of conductive hearing loss may also be treated by surgical procedures.

Sensorineural hearing loss, on the other hand, is caused by the absence or destruction of the hair cells in the cochlea which are needed to transduce acoustic signals into auditory nerve impulses. People who suffer from sensorineural hearing loss may be unable to derive significant benefit from conventional hearing aid systems, no matter how loud the acoustic stimulus is. This is because the mechanism for transducing sound energy into auditory nerve impulses has been damaged. Thus, in the absence of properly functioning hair cells, auditory nerve impulses cannot be generated directly from sounds.

To overcome sensorineural hearing loss, numerous auditory prosthesis systems (e.g., cochlear implant systems) have been developed. Auditory prosthesis systems bypass the hair cells in the cochlea by presenting electrical stimulation directly to the auditory nerve fibers. Direct stimulation of the auditory nerve fibers leads to the perception of sound in the brain and at least partial restoration of hearing function.

Conventional auditory prosthesis systems include a sound processing unit worn on or behind the ear of a patient. The sound processing unit typically includes a microphone for detecting sounds in the patient's environment and audio processing circuitry for modifying, digitizing, and/or amplifying the detected sounds. As such, sound processing units worn behind or on the ear are often relatively large, cumbersome, and noticeable by others. They often lack desirable features (e.g., extended battery life and optimal sound processing capabilities) because such features would make them even larger and more cumbersome.

Hence, sound processing units have been developed that may be worn by a patient off the ear (e.g., secured to a piece of clothing worn by the patient, carried in a pocket or pouch, and/or otherwise carried by the patient). However, conventional sound processing units configured to be worn off the ear lack the ability to selectively interface with a telecoil and/or an auxiliary microphone positioned proximal to the ear canal of the patient.

SUMMARY

An exemplary apparatus for use with an auditory prosthesis system includes 1) a housing, 2) a connector port disposed at least partially within the housing and configured to be communicatively coupled to an auxiliary audio input device, 3) a telecoil disposed at least partially within the housing, and 4) a multi-position switch disposed at least partially within the housing and configured to selectively enable the auxiliary audio input device and the telecoil. The auxiliary audio input device is enabled and the telecoil is disabled when the switch is in a first position, both the auxiliary audio input device and the telecoil are enabled when the switch is in a second position, and the telecoil is enabled and the auxiliary audio input device is disabled when the switch is in a third position.

An exemplary system includes 1) an auditory prosthesis configured to be implanted in a patient, 2) a sound processor module configured to process a plurality of audio signals and direct the auditory prosthesis to apply stimulation representative of the plurality of audio signals to one or more stimulation sites within the patient, 3) a headpiece configured to facilitate communication between the sound processor module and the auditory prosthesis, 4) a modular adapter assembly configured to be selectively coupled in series between the sound processor module and the headpiece, the modular adapter assembly including a telecoil disposed therein, and 5) an auxiliary microphone communicatively coupled to the modular adapter assembly and configured to selectively detect one or more of the audio signals when the auxiliary microphone is enabled. The modular adapter assembly is further configured facilitate selective enablement of the auxiliary microphone and the telecoil.

An exemplary method includes 1) providing a modular adapter assembly comprising a multi-position switch for use in an auditory prosthesis system, the multi-position switch configured to selectively be in one of a first position, a second position, and a third position, 2) selectively enabling an auxiliary audio input device communicatively coupled to the modular adapter assembly and disabling a telecoil included in the modular adapter assembly in response to a positioning of the switch in the first position, 3) selectively enabling both the auxiliary audio input device and the telecoil in response to a positioning of the switch in the second position, and 4) selectively disabling the auxiliary audio input device and enabling the telecoil in response to a positioning of the switch in the third position.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

An exemplary modular adapter assembly for telecoil and auxiliary audio input device mixing is described herein. As will be described below, the exemplary modular adapter assembly may include a housing, a connector port disposed at least partially within the housing and configured to be communicatively coupled to an auxiliary audio input device (e.g., an auxiliary microphone such as a T-MIC by Advanced Bionics, LLC), a telecoil disposed at least partially within the housing, and a multi-position switch disposed at least partially within the housing and configured to selectively enable the auxiliary audio input device and the telecoil. When the switch is in a first position, the auxiliary audio input device is enabled and the telecoil is disabled. When the switch is in a second position, both the auxiliary audio input device and the telecoil are enabled. When the switch is in a third position, the telecoil is enabled and the auxiliary audio input device is disabled.

The modular adapter assembly described herein may be used within an auditory prosthesis system that includes an auditory prosthesis (e.g., a cochlear implant) configured to be implanted in a patient, a sound processor module configured to process a plurality of audio signals and direct the auditory prosthesis to apply stimulation representative of the plurality of audio signals to one or more stimulation sites within the patient, and a headpiece configured to facilitate communication between the sound processor module and the auditory prosthesis. As described below, the modular adapter assembly may be coupled in series between the sound processor module and the headpiece in order to facilitate selective use of a telecoil and an auxiliary audio input device in response to user actuation of the multi-position switch.

Numerous advantages may be associated with the modular adapter assembly described herein. For example, the modular adapter assembly may facilitate selective use by a patient of an auxiliary microphone and/or a telecoil in conjunction with an auditory prosthesis system worn by the patient. This may result in enhanced performance of the auditory prosthesis system, simple and convenient expansion and removal of features associated with the auditory prosthesis system, and a more functional and aesthetically pleasing experience for a user of the auditory prosthesis system.

Figure 1:
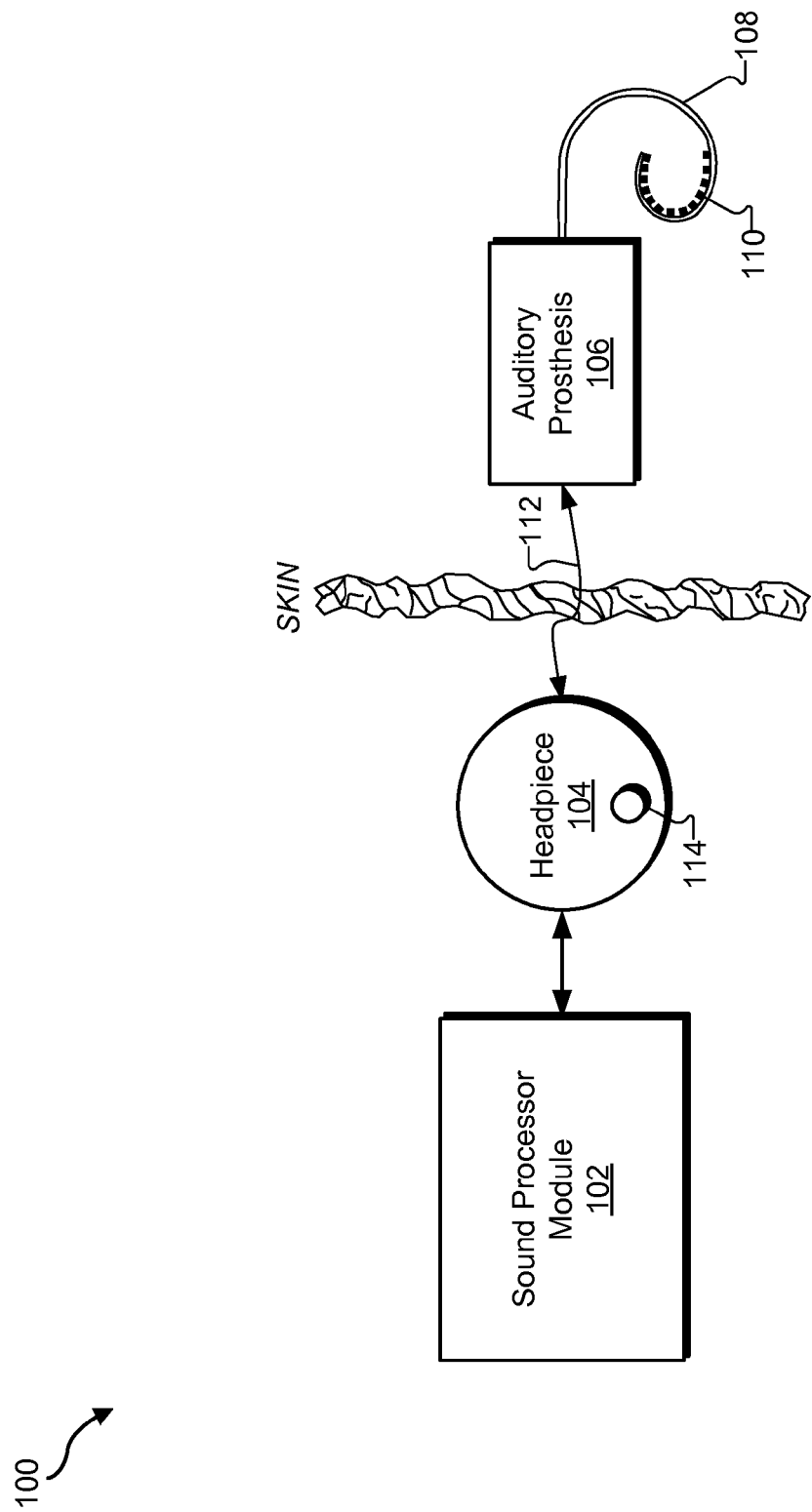
FIG. 1 illustrates an exemplary auditory prosthesis system according to principles described herein.

FIG. 1 illustrates an exemplary auditory prosthesis system 100. Auditory prosthesis system 100 may include a sound processor module 102, a headpiece 104, and an auditory prosthesis 106. Auditory prosthesis system 100 may further include a lead 108 coupled to auditory prosthesis 106 and having a plurality of electrodes 110 disposed thereon. As shown in FIG. 1, sound processor module 102 and headpiece 104 may be located external to an auditory prosthesis patient. Auditory prosthesis 106, lead 108, and electrodes 110 may be implanted within the patient. As will be described in more detail below, additional or alternative components may be included within auditory prosthesis system 100 as may serve a particular implementation.

In some examples, sound processor module 102 is configured to be worn off the ear of a patient. In other words, sound processor module 102 may be worn or carried by a patient at any location other than behind or on the ear. For example, sound processor module 102 may be secured to a piece of clothing worn by the patient, carried in a pocket or pouch, and/or otherwise carried by the patient. Because sound processor module 102 is not worn behind or on the ear, sound processor module 102 may be relatively larger than typical behind-the-ear sound processors and may therefore include additional or enhanced features compared to such typical behind-the-ear sound processors. For example, sound processor module 102 may be coupled to one or more accessory headers each providing one or more additional features and/or capabilities to sound processor module 102. In some examples, sound processor module 102 is water proof or at least water resistant.

Sound processor module 102 may be configured to operate in accordance with a plurality of control parameters. As used herein, a "control parameter" may include any parameter governing an operation of sound processor module 102. Exemplary control parameters include, but are not limited to, volume control parameters, microphone sensitivity parameters, program selection parameters, noise reduction parameters, microphone direction parameters, pitch parameters, timbre parameters, sound quality parameters, most comfortable current levels ("M levels"), threshold current levels, channel acoustic gain parameters, front and backend dynamic range parameters, current steering parameters, pulse rate values, pulse width values, frequency parameters, amplitude parameters, waveform parameters, electrode polarity parameters (i.e., anode-cathode assignment), location parameters (i.e., which electrode pair or electrode group receives the stimulation current), stimulation type parameters (i.e., monopolar, bipolar, or tripolar stimulation), burst pattern parameters (e.g., burst on time and burst off time), duty cycle parameters, spectral tilt parameters, filter parameters, and dynamic compression parameters.

To illustrate, sound processor module 102 may process an audio signal (which may be detected by a microphone, input by way of an auxiliary audio input port, etc.) in accordance with one or more control parameters (e.g., that may be associated with a particular sound processing strategy). Sound processor module 102 may then direct auditory prosthesis 106 to generate and apply electrical stimulation (also referred to herein as "stimulation current") representative of the audio signal to one or more stimulation sites associated with an auditory pathway (e.g., the auditory nerve) of the patient. Exemplary stimulation sites include, but are not limited to, one or more locations within the cochlea, the cochlear nucleus, the inferior colliculus, and/or any other nuclei in the auditory pathway.

In some examples, sound processor module 102 may wirelessly transmit stimulation parameters and/or power signals to auditory prosthesis 106 by way of a communication link 112 between headpiece 104 and auditory prosthesis 106. It will be understood that communication link 112 may include a bi-directional communication link and/or one or more dedicated uni-directional communication links. In some alternative embodiments, sound processor module 102 and auditory prosthesis 106 may be directly connected with one or more wires or the like.

Headpiece 104 may be configured to be affixed to a patient's head and positioned such that a coil housed within headpiece is communicatively coupled to a corresponding coil included within auditory prosthesis 106. In this manner, control parameters and power signals may be wirelessly transmitted between sound processor module 102 and auditory prosthesis 106 via communication link 112.

Headpiece 104 may further include a microphone 114, which may be selectively used to detect one or more audio signals for processing by sound processor module 102. Headpiece 104 may include additional or alternatively components as may serve a particular implementation.

Auditory prosthesis 106 may include any type of implantable stimulator that may be used in association with the systems and methods described herein. For example, auditory prosthesis 106 may include an implantable cochlear stimulator. In some alternative implementations, auditory prosthesis 106 may include a brainstem implant and/or any other type of auditory prosthesis that may be implanted within a patient and configured to apply stimulation to one or more stimulation sites located along an auditory pathway of a patient.

In some examples, auditory prosthesis 106 may be configured to generate electrical stimulation representative of an audio signal detected by microphone 102 in accordance with one or more stimulation parameters transmitted thereto by sound processor module 102. Auditory prosthesis 106 may be further configured to apply the electrical stimulation to one or more stimulation sites within the patient via one or more electrodes 110 disposed along lead 108. In some examples, auditory prosthesis 106 may include a plurality of independent current sources each associated with a channel defined by one or more of electrodes 110. In this manner, different stimulation current levels may be applied to multiple stimulation sites simultaneously by way of multiple electrodes 110. In such examples, auditory prosthesis system 100 may be referred to as a "multi-channel auditory prosthesis system."

Figure 2:
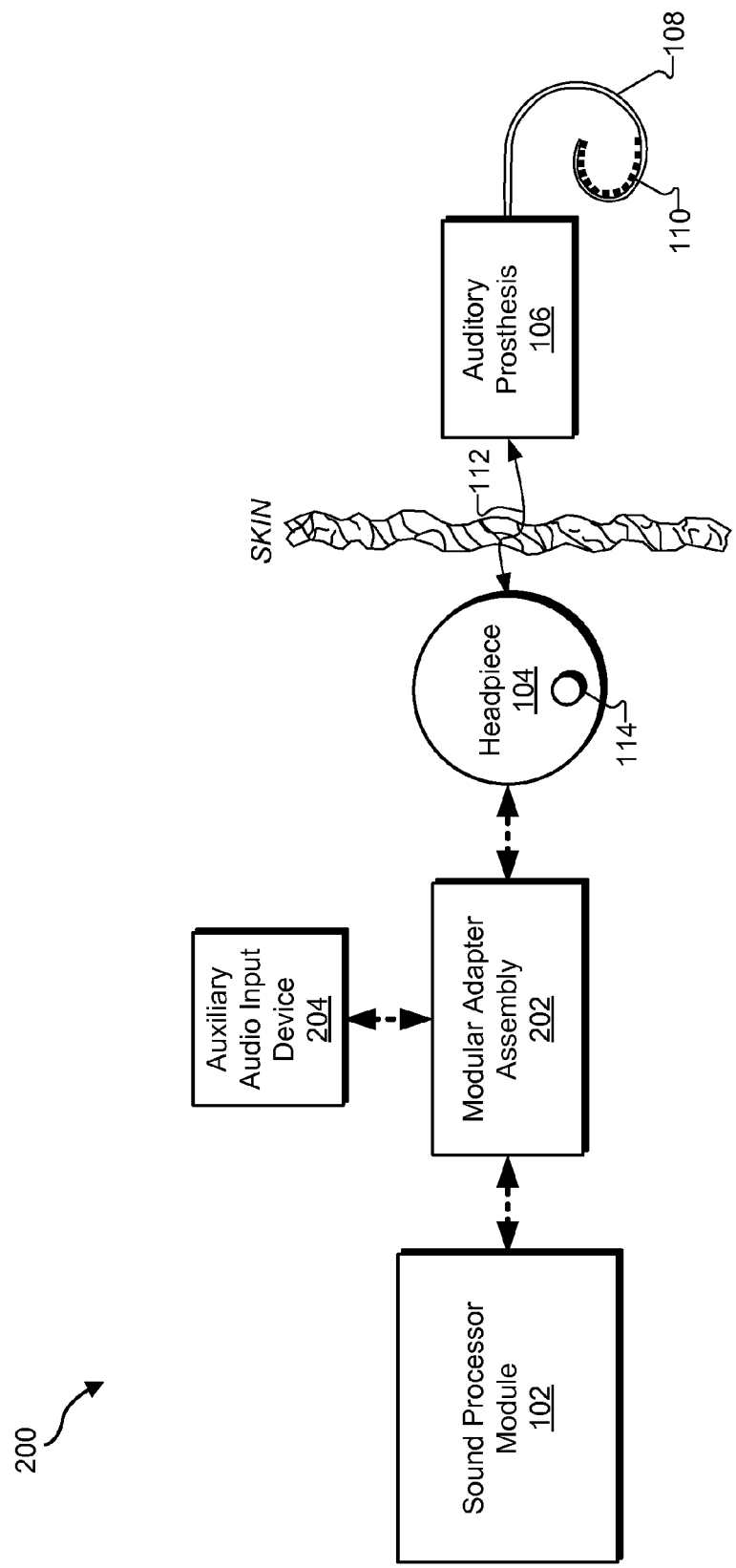
FIG. 2 illustrates an exemplary implementation of the auditory prosthesis system of FIG. 1 according to principles described herein.

FIG. 2 illustrates an exemplary implementation 200 of auditory prosthesis system 100 in which a modular adapter assembly 202 is configured to be selectively coupled in series between sound processor module 102 and headpiece 104. As shown, modular adapter assembly 202 may be additionally coupled to an auxiliary audio input device 204. An exemplary auxiliary audio input device 204 includes an auxiliary microphone, such as a T-MIC by Advanced Bionics, LLC, that may be positioned proximal to an ear canal of a patient. Alternatively, auxiliary audio input device 204 may include an audio player (e.g., an MP3 player), an FM transmitter, and/or any other device configured to provide audio input that may be processed by sound processor module 102. In the examples provided herein, it will be assumed that auxiliary audio input device 204 includes an auxiliary microphone.

As illustrated by the dashed lines in FIG. 2, modular adapter assembly 202 may be configured to be selectively coupled to sound processor module 102, headpiece 104, and/or auxiliary audio input device 204. In this manner, a patient may selectively use modular adapter assembly 202 in certain situations and not in others.

Figure 3:
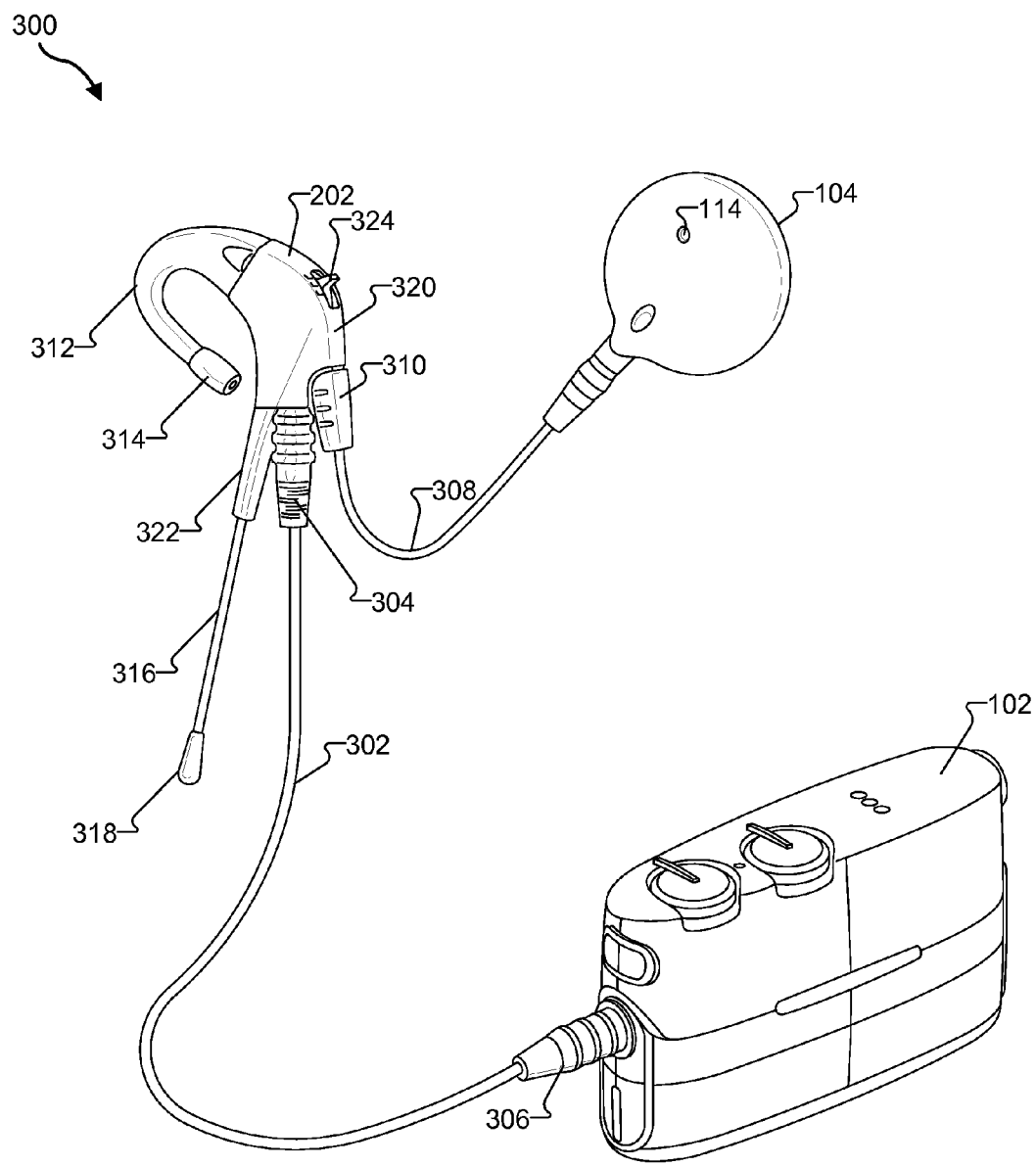
FIG. 3 illustrates an exemplary perspective view of a modular adapter assembly coupled in series between a sound processor module and a headpiece according to principles described herein.

FIG. 3 illustrates an exemplary perspective view 300 of modular adapter assembly 202 coupled in series between sound processor module 102 and headpiece 104. Modular adapter assembly 202 may be coupled to sound processor module 102 and headpiece 104 in any suitable manner. For example, as shown in FIG. 3, modular adapter assembly 202 may be coupled to sound processor module 102 by way of cable 302. To this end, modular adapter assembly 202 and sound processor module 102 may each include a connector port (not shown) configured to connect to corresponding connectors 304 and 306 of cable 302. Likewise, modular adapter assembly 202 may be coupled to headpiece 104 by way of cable 308. To this end, modular adapter assembly 202 may include another connector port (not shown) configured to connect to a corresponding connector 310 of cable 308. When a user desires to bypass modular adapter assembly 202, he or she may remove connector 306 of cable 302 from the connector port of sound processor module 102 and instead connect connector 310 of cable 308 to the connector port of sound processor module 102.

As illustrated in FIG. 3, modular adapter assembly 202 may be selectively coupled to an ear hook 312 comprising an auxiliary microphone 314 disposed at a distal end thereof. In some examples, ear hook 312 may be dimensioned such that ear hook 312 and modular adapter assembly 202 may be worn on and/or behind the ear of a patient and so that auxiliary microphone 314 may be positioned proximate to the ear canal of the patient.

Modular adapter assembly 202 may also be coupled to a formable wire 316. Formable wire 316 may be made out of any suitable material and may be used to secure modular adapter assembly 202 in place behind the ear of a patient. For example, formable wire 316 may be wrapped around the ear of a patient in order to secure modular adapter assembly 202 in place behind the ear of the patient. In some embodiments, as shown in FIG. 3, formable wire 316 may include a knob 318 at a distal end thereof. Knob 318 may be made out of any suitable material and is configured to prevent formable wire 316 from digging into, cutting, or otherwise bothering the patient's skin.

In some examples, formable wire 316 may be selectively coupled to modular adapter assembly 202 by way of a rail system included within modular adapter assembly 202. For example, a housing 320 of modular adapter assembly 202 may include one or more rails disposed on an inner surface thereof. The rails may be configured to form a receptacle into which a connector 322 of formable wire 316 may be inserted. Any suitable locking mechanism may secure connector 322 within the receptacle formed by the one or more rails. It will be recognized that any other suitable connecting means may be used to couple formable wire 316 to modular adapter assembly 202 as may serve a particular implementation.

As mentioned, modular adapter assembly 202 may be configured to facilitate selective enablement of auxiliary microphone 314 and of a telecoil disposed within the housing 320 of modular adapter assembly 202. To this end, modular adapter assembly 202 may include mixing circuitry within housing 320 and a multi-position switch 324 that may be accessible to a user (e.g., by being at least partially disposed on an outer surface of housing 320) and used by the user to switch between different enablement modes. For example, a user may move switch 324 to a first position to enable auxiliary microphone 314 and disable the telecoil, to a second position to enable both the auxiliary microphone 314 and the telecoil, and to a third position to enable the telecoil and disable auxiliary microphone 314.

In some examples, an enabled auxiliary microphone 314 overrides microphone 114 included in headpiece 104. In other words, when auxiliary microphone 314 is enabled, sound processor module 102 processes audio signals detected by auxiliary microphone 314 instead of audio signals detected by microphone 114. However, when auxiliary microphone 314 is disabled, sound processor module 102 processes audio signals detected by microphone 114 instead of auxiliary microphone 314.

Figure 4:
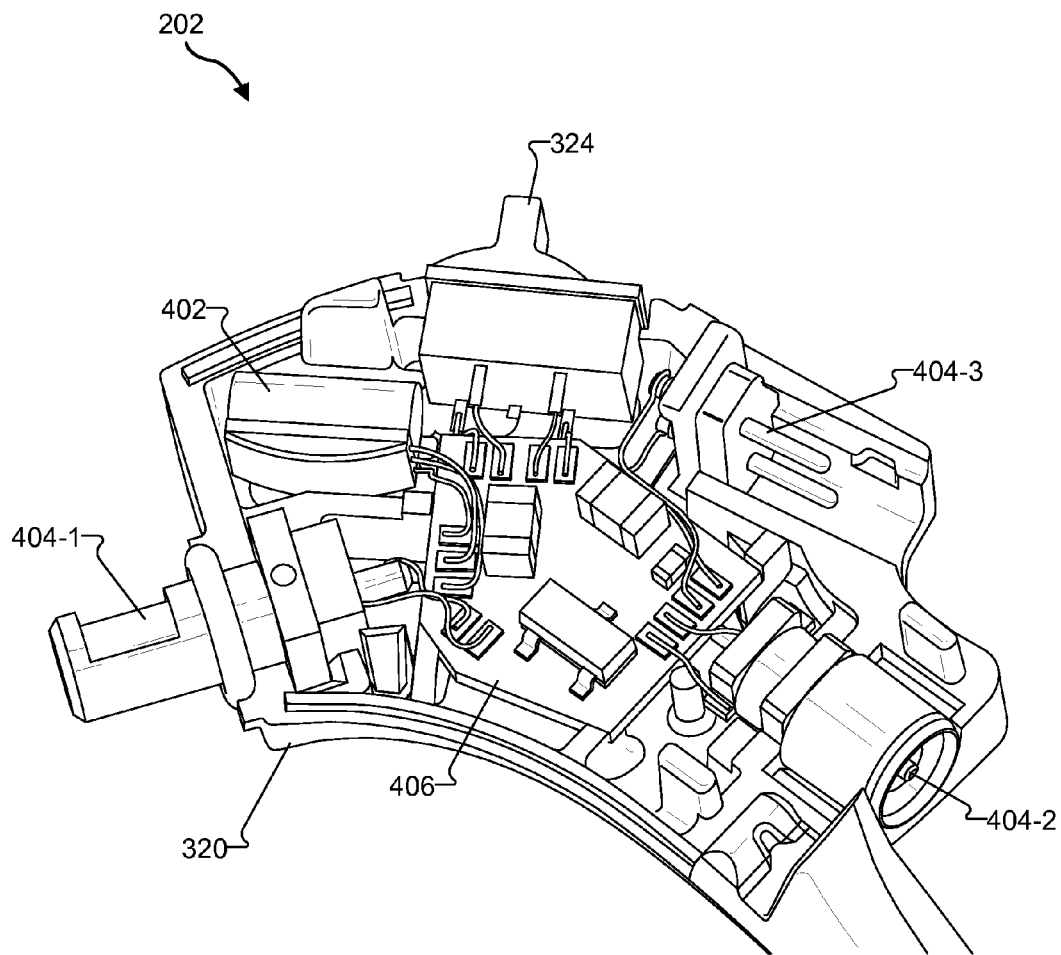
FIG. 4 illustrates an exemplary top perspective view of components at least partially disposed within a housing of a modular adapter assembly according to principles described herein.

FIG. 4 illustrates an exemplary top perspective view of components at least partially disposed within the housing 320 of modular adapter assembly 202. As shown, housing 320 may include switch 324, a telecoil 402, a plurality of connector ports 404 (e.g., connector ports 404-1 through 404-3), and a printed circuit board 406 at least partially disposed therein. Each of these components will now be briefly described.

As described above, switch 324 may be configured to facilitate selective enablement of telecoil 402 and auxiliary audio input device 204. To this end, switch 324 may be configured to be placed in three or more different positions in response to actuation thereof by a user.

Telecoil 402 may include any suitable components configured to provide telecoil functionality. In some examples, including telecoil 402 within modular adapter assembly 202 instead of within sound processor module 102 may minimize interference between the processing components of sound processor module 102 and telecoil 402 and thereby optimize telecoil performance.

Connector ports 404 may be configured to facilitate selective coupling of modular adapter assembly 202 to auxiliary audio input device 204, sound processor module 102, and headpiece 104. For example, connector port 404-1 may be configured to couple to an ear hook (e.g., ear hook 312) that includes an auxiliary microphone (e.g., auxiliary microphone 314), connector port 404-2 may be configured to connect to sound processor module 102 (e.g., by connecting to connector 304 of cable 302), and connector port 404-3 may be configured to connect to headpiece 104 (e.g. by connecting to connector 310 of cable 308). It will be recognized that connector ports 404 may each include any suitable type of connector port as may serve a particular implementation.

Printed circuit board 406 may include various electrical components (e.g., one or more capacitors, inductors, transistors, resistors, etc.) configured to facilitate telecoil and auxiliary audio input device mixing. Exemplary components configured to facilitate telecoil an auxiliary audio input device mixing will be described in more detail below.

Figure 5:
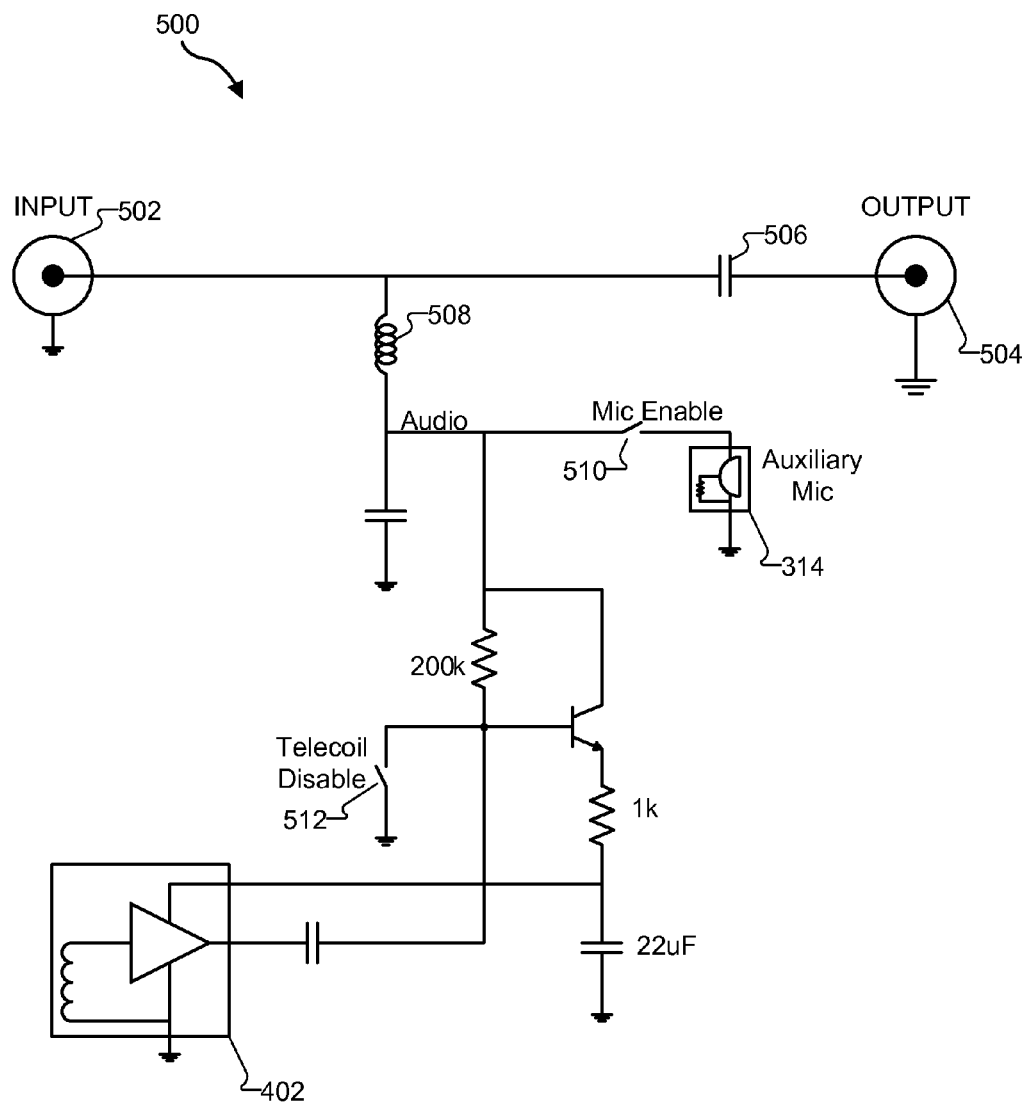
FIG. 5 illustrates an exemplary circuit diagram of various components included within a modular adapter assembly according to principles described herein.

FIG. 5 illustrates an exemplary circuit diagram 500 of various components included within modular adapter assembly 202. For illustrative purposes, it will be assumed in the example given in connection with FIG. 5 that modular adapter assembly 202 is configured to selectively enable auxiliary microphone 314 and/or telecoil 402. Hence, it will be recognized that the circuit diagram shown in FIG. 5 is merely illustrative of the many different circuit implementations of modular adapter assembly 202.

Circuit diagram 500 shows that modular adapter assembly 202 may include an input port 502 configured to receive signals from sound processor module 102, an output port 504 configured to pass signals to headpiece 104, a capacitor 506, an inductor 508, a microphone enable switch 510, a telecoil disable switch 512, telecoil 402, and various other electrical components configured to facilitate telecoil and auxiliary microphone mixing.

Input port 502 may be implemented by connector port 404-2 and may be configured to receive signals from the sound processor module 102. For example, input port 502 may receive a DC power signal (e.g., a 2.7 volt DC power signal) configured to provide power telecoil 402, auxiliary microphone 314, and other electrical components included within modular adapter assembly 202. Input port 502 may be further configured to receive a high frequency communication signal (e.g., a 49 MHz signal) intended for auditory prosthesis 106.

In some examples, modular adapter assembly 202 may be configured to pass the high frequency communication signal to headpiece 104 and prevent the DC power signal from being passed to headpiece 104. To this end, blocking capacitor 506 is placed in series between input port 502 and output port 504 (which may be implemented by connector port 404-3). As will be appreciated, blocking capacitor 506 allows the high frequency communications signal to pass to headpiece 104 by way of output port 504 and prevents the DC power signal from being passed to headpiece 104 by way of output port 504.

Modular adapter assembly 202 may be further configured to block the high frequency communication signal from being passed to telecoil 402 and auxiliary microphone 314. To this end, inductor 508 may be included within circuit diagram 500 as shown in FIG. 5. As will be appreciated, inductor 508 allows the DC power signal to pass to telecoil 402 and auxiliary microphone 314 and prevents the high frequency communication signal from being passed to telecoil 402 and auxiliary microphone 314.

Microphone enable switch 510 may be configured to enable auxiliary microphone 314 by selectively providing operating power (e.g., when microphone enable switch 510 is in a closed position) to auxiliary microphone 314. Likewise, telecoil disable switch 512 may be configured to enable telecoil 402 by selectively providing operating power (e.g., when telecoil disable switch 512 is in an open position) to telecoil 402. Microphone enable switch 510 and telecoil disable switch 512 may be implemented by switch 324. For example, if a user moves switch 324 to a first position, this may cause both microphone enable switch 510 and telecoil disable switch 512 to be closed, thereby enabling only auxiliary microphone 314. However, if the user moves switch 324 to a second position, this may cause microphone enable switch 510 to be closed and telecoil disable switch 512 to be open, thereby enabling both auxiliary microphone 314 and telecoil 402. Finally, if the user moves switch 324 to a third position, this may cause both microphone enable switch 510 and telecoil disable switch 512 to be open, thereby enabling only telecoil 402.

Figure 6:
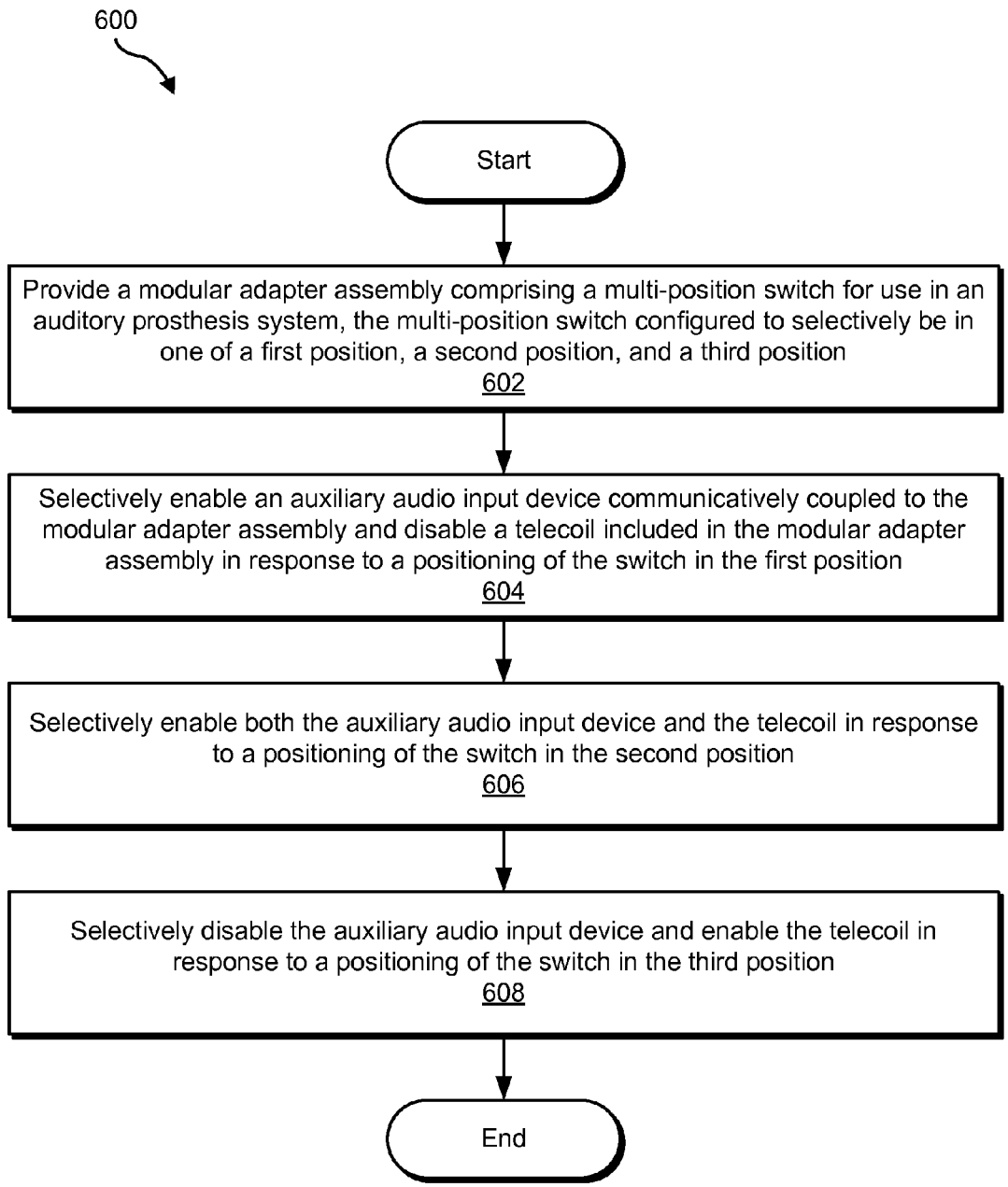
FIG. 6 illustrates an exemplary method of facilitating telecoil and auxiliary audio input device mixing according to principles described herein.

FIG. 6 illustrates an exemplary method 600 of facilitating telecoil and auxiliary audio input device mixing. While FIG. 6 illustrates exemplary steps according to one embodiment, other embodiments may omit, add to, reorder, and/or modify any of the steps shown in FIG. 6. One or more of the steps shown in FIG. 6 may be performed by modular adapter assembly 202.

In step 602, a modular adapter assembly is provided that comprises a multi-position switch for use in an auditory prosthesis system. The multi-position switch may be configured to selectively be in one of a first position, a second position, and a third position.

In step 604, an auxiliary audio input device communicatively coupled to the modular adapter assembly is selectively enabled and a telecoil included in the modular adapter assembly is selectively disabled in response to a positioning of the switch in the first position.

In step 606, both the auxiliary audio input device and the telecoil are selectively enabled in response to a positioning of the switch in the second position.

In step 608, the auxiliary audio input device is selectively disabled and the telecoil is selectively enabled in response to a positioning of the switch in the third position.

In certain embodiments, one or more of the processes described herein may be implemented at least in part as instructions executable by one or more computing devices. In general, a processor (e.g., a microprocessor) receives instructions, from a tangible computer-readable medium, (e.g., a memory, etc.), and executes those instructions, thereby performing one or more processes, including one or more of the processes described herein. Such instructions may be stored and/or transmitted using any of a variety of known non-transitory computer-readable media.

A non-transitory computer-readable medium (also referred to as a processor-readable medium) includes any non-transitory medium that participates in providing data (e.g., instructions) that may be read by a computer (e.g., by a processor of a computer). Such a non-transitory medium may take many forms, including, but not limited to, non-volatile media and/or volatile media. Non-volatile media may include, for example, optical or magnetic disks and other persistent memory. Volatile media may include, for example, dynamic random access memory ("DRAM"), which typically constitutes a main memory. Common forms of non-transitory computer-readable media include, for example, a floppy disk, flexible disk, hard disk, magnetic tape, any other magnetic medium, a CD-ROM, DVD, any other optical medium, a RAM, a PROM, an EPROM, a FLASH-EEPROM, any other memory chip or cartridge, or any other non-transitory medium from which a computer can read.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. An apparatus for use with an auditory prosthesis system, the apparatus comprising:
    a housing configured to be worn behind an ear of a patient;
    a first connector port disposed at least partially within the housing and configured to be communicatively coupled to an auxiliary audio input device disposed on an ear hook that connects to the first connector port;
    a second connector port disposed at least partially within the housing and configured to be communicatively coupled, by way of a first cable, to a sound processor module configured to be worn off the ear of the patient;
    a third connector port disposed at least partially within the housing and configured to be communicatively coupled, by way of a second cable, to a headpiece, the headpiece configured to communicate with an auditory prosthesis implanted within the patient;
    a telecoil disposed at least partially within the housing; and
    a multi-position switch disposed at least partially within the housing and configured to selectively enable the auxiliary audio input device and the telecoil;
    wherein the auxiliary audio input device is enabled and the telecoil is disabled when the switch is in a first position, both the auxiliary audio input device and the telecoil are enabled when the switch is in a second position, and the telecoil is enabled and the auxiliary audio input device is disabled when the switch is in a third position; and
    wherein the apparatus is configured to facilitate communication between the sound processor module and the auditory prosthesis by way of the first and second cables.

2. The apparatus of claim 1, wherein the apparatus receives, from the sound processor module by way of the second connector port and the first cable, a DC power signal configured to selectively provide power to the auxiliary audio input device and the telecoil, and wherein the apparatus further comprises:
    a capacitor configured to prevent the DC power signal from being passed to the headpiece by way of the third connector port and the second cable; and
    an inductor configured to pass the DC power signal to at least one of the auxiliary audio input device and the telecoil.

3. The apparatus of claim 2, wherein:
    the apparatus further receives, from the sound processor module by way of the second connector port, a high frequency communication signal intended for the auditory prosthesis;
    the capacitor is further configured to allow the high frequency communication signal to pass to the headpiece for transmission to the auditory prosthesis; and
    the inductor is further configured to block the high frequency communication signal from being passed to the auxiliary audio input device and the telecoil.

4. The apparatus of claim 1, wherein the switch is configured to selectively enable the auxiliary audio input device and the telecoil by selectively providing operating power to the auxiliary audio input device and the telecoil.

5. The apparatus of claim 1, wherein at least a portion of the switch is disposed on an outer surface of the housing and is configured to be selectively positioned within one of the three positions by a user.

6. The apparatus of claim 1, wherein the auxiliary audio input device comprises an auxiliary microphone.

7. A system comprising:
    an auditory prosthesis configured to be implanted in a patient;
    a sound processor module configured to be worn off an ear of the patient and to process a plurality of audio signals and direct the auditory prosthesis to apply stimulation representative of the plurality of audio signals to one or more stimulation sites within the patient;
    a headpiece configured to facilitate communication between the sound processor module and the auditory prosthesis;
    an auxiliary microphone disposed on an ear hook and that is configured to selectively detect one or more of the audio signals when the auxiliary microphone is enabled; and
    a modular adapter assembly configured to be worn behind the ear of the patient and comprising
        a housing,
        a first connector port disposed at least partially within the housing and configured to be communicatively coupled to the auxiliary microphone while connected to the ear hook,
        a second connector port disposed at least partially within the housing and configured to be communicatively coupled, by way of a first cable, to the sound processor module,
        a third connector port disposed at least partially within the housing and configured to be communicatively coupled, by way of a second cable, to the headpiece,
        a telecoil disposed at least partially within the housing, and
        a multi-position switch disposed at least partially within the housing and configured to selectively enable the auxiliary microphone and the telecoil;
    wherein the modular adapter assembly is further configured to facilitate communication between the sound processor module and the auditory prosthesis by way of the first and second cables.

8. The system of claim 7, wherein the headpiece comprises an additional microphone configured to detect one or more of the audio signals when the auxiliary microphone is disabled.

9. The system of claim 7, wherein the multi-position switch is configured to facilitate selective enablement of the auxiliary microphone and the telecoil by selectively providing operating power to the auxiliary audio input device and the telecoil.

10. The system of claim 7, wherein:
    the auxiliary microphone is enabled and the telecoil is disabled when the switch is in a first position, both the auxiliary microphone and the telecoil are enabled when the switch is in a second position, and the telecoil is enabled and the auxiliary microphone is disabled when the switch is in a third position.

11. The system of claim 10, wherein at least a portion of the switch is disposed on an outer surface of the modular adapter assembly and is configured to be selectively positioned within one of the three positions by a user.

12. The system of claim 7, wherein the modular adapter assembly receives, from the sound processor module, a DC power signal configured to selectively provide power to the auxiliary audio input device and the telecoil, and wherein the modular adapter assembly comprises:
- a capacitor configured to prevent the DC power signal from being passed to the headpiece port; and
- and an inductor configured to pass the DC power signal to at least one of the auxiliary microphone and the telecoil.

13. The system of claim 12, wherein:
- the modular adapter assembly further receives, from the sound processor module, a high frequency communication signal intended for the auditory prosthesis;
- the capacitor is further configured to allow the high frequency communication signal to pass to the headpiece for transmission to the auditory prosthesis; and
- the inductor is further configured to block the high frequency communication signal from being passed to the auxiliary microphone and the telecoil.

* * * * *